United States Patent
Rodenberg et al.

(10) Patent No.: US 8,323,658 B2
(45) Date of Patent: *Dec. 4, 2012

(54) INFECTIOUS BURSAL DISEASE VIRUS ANTIGENIC ISOLATES AND VACCINES

(75) Inventors: Jeffrey Harold Rodenberg, Fort Dodge, IA (US); Mahesh Kumar, Fort Dodge, IA (US); Kalen Cookson, Lawrenceville, GA (US)

(73) Assignee: PAH W LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/914,591

(22) Filed: Oct. 28, 2010

(65) Prior Publication Data

US 2011/0123560 A1 May 26, 2011

Related U.S. Application Data

(63) Continuation of application No. 11/811,222, filed on Jun. 8, 2007, now abandoned, which is a continuation of application No. 11/076,713, filed on Mar. 10, 2005, now Pat. No. 7,338,661.

(60) Provisional application No. 60/552,989, filed on Mar. 12, 2004.

(51) Int. Cl.
- *A61K 39/12* (2006.01)
- *A61K 39/295* (2006.01)
- *C07K 14/08* (2006.01)
- *C12N 7/00* (2006.01)

(52) U.S. Cl. ............... 424/186.1; 424/204.1; 424/202.1; 530/350; 435/235.1

(58) Field of Classification Search ......................... None
See application file for complete search history.

(56) References Cited

U.S. PATENT DOCUMENTS

| | | | |
|---|---|---|---|
| 4,530,831 A * | 7/1985 | Lutticken et al. | 424/202.1 |
| 5,192,539 A | 3/1993 | van Der Marel et al. | |
| 5,595,912 A | 1/1997 | Vakharia et al. | |
| 5,605,792 A | 2/1997 | Jackwood et al. | |
| 5,605,827 A * | 2/1997 | Jackwood et al. | 435/235.1 |
| 5,614,409 A * | 3/1997 | Azad et al. | 435/252.3 |
| 5,804,195 A | 9/1998 | Gutter | |
| 5,919,461 A * | 7/1999 | van der Marel et al. | 424/204.1 |
| 6,471,962 B1 | 10/2002 | Snyder | |
| 7,338,661 B2 * | 3/2008 | Rodenberg et al. | 424/204.1 |

FOREIGN PATENT DOCUMENTS

| | | |
|---|---|---|
| WO | WO 9105569 | 5/1991 |
| WO | WO 9116925 A1 | 11/1991 |
| WO | WO 00/29016 | 5/2000 |
| WO | WO2004/085634 A2 | 10/2004 |

OTHER PUBLICATIONS

Banda et al (Avian Diseases 45:620-630, 2001).*
Sellers et al (Avian Diseases 43: 198-206, 1999).*
Jackwood et al (Avian Diseases 45:330-339, 2001).*
Lana et al (Virus Genes 6:247-259, 1992).*
Breedervac-Reo-Plus product information sheet, Intervet, 2002.*
Genbank AAM21068.1, 2002.*
Pitcovski, J. et al., 2003, "Development and large-scale use of recombinant VP2 vaccine for the prevention of infectious bursal disease or chickens," Vaccine, vol. 21, pp. 4736-4743.
Martinez-Torrecuadrada, J. L. et al., 2003, "Structure-dependent efficacy of infectious bursal disease virus (IBDV) recombinant vaccines," Vaccine, vol. 21, pp. 3342-3350.
Domanska, K. et al., 2004, "Antigenic and genetic diversity of early European isolates of *Infectious bursal disease virus* prior to the emergence of the very virulent viruses: early European epidemiology of *Infectious bursal disease virus* revisited?" , Archives of Virology, vol. 149, pp. 465-480.
Avian Disease, 41, 627-637, 1997, Restriction Fragment Length Polymorphisms in the VP2 Gene of Infectious Bursal Disease Viruses, Jackwood et al.
Avian Disease, 45, 330-339, 2001, Amino Acid Comparison of Infectious Bursal Disease Viruses Placed in the Same and Different Molecular Groups by RT/PCR-RFLP, Jackwood et al.
Results of SEQ ID No. 6 search, .rag (Jun. 19, 2006).
Hilgers et al., "Effect of various adjuvants on secondary immune respone in chickens, "Veterinary Immunology and Immunopathology, 66 (1998), pp. 159-171.
Muller et al., "Research on infectious bursal disease—the past, the present and the future," Veterina Microbiology, 97 (2003) 153-165.
Banda et al. Avian Diseases 45:620-630, 2001.
Sellers et al. Avian Diseases 43: 198-206, 1999.
Zierenberg et al. Archives of Virology, 2000, vol. 145, No. 1, pp. 113-125.
Guo et al. Avian Diseases , 2003, vol. 47, No. 4, pp. 1423-1481.
Fahey et al. Journal of Gene al Virology, 1989, vol. 70, No. 6, pp. 1473-1481.
Sharma et al. Avian Diseases, 1985, vol. 29, No. 4, pp. 1155-1169.

* cited by examiner

*Primary Examiner* — Mary E Mosher
(74) *Attorney, Agent, or Firm* — Kelly M. Sullivan (57) ABSTRACT

Antigenic isolates and vaccines for Infectious Bursal Disease Virus include variants of the molecular Group 6 family of IBDV isolates, in particular the 28-1 isolate.

9 Claims, 4 Drawing Sheets

SEQUENCE LISTING

```
<160> NUMBER OF SEQ ID NOS: 6

<210> SEQ ID NO 1
<211> LENGTH: 123
<212> TYPE: PRT
<213> ORGANISM: Virus

<400> SEQUENCE: 1

Ala Ala Asp Asp Tyr Gln Phe Ser Ser Gln Tyr Gln Pro Gly Gly Val
1               5                   10                  15

Thr Ile Thr Leu Phe Ser Ala Asn Ile Asp Ala Ile Thr Ser Leu Ser
            20                  25                  30
```

-continued

Val Gly Gly Glu Leu Val Phe Gln Thr Ser Val Gln Gly Leu Val Leu
            35                  40                  45

Gly Ala Thr Ile Tyr Leu Ile Gly Phe Asp Gly Thr Ala Val Ile Thr
        50                  55                  60

Arg Ala Val Ala Ala Asp Asn Gly Leu Thr Ala Gly Thr Asp Asn Leu
65                  70                  75                  80

Met Pro Phe Asn Leu Val Ile Pro Thr Asn Glu Ile Thr Gln Pro Ile
                85                  90                  95

Thr Ser Ile Lys Leu Glu Ile Val Thr Ser Lys Ser Gly Gly Gln Ala
            100                 105                 110

Gly Asp Gln Met Ser Trp Ser Ala Ser Gly Ser
        115                 120

<210> SEQ ID NO 2
<211> LENGTH: 123
<212> TYPE: PRT
<213> ORGANISM: Virus

<400> SEQUENCE: 2

Ala Ala Asp Asp Tyr Gln Phe Ser Ser Gln Tyr Gln Pro Gly Gly Val
1               5                   10                  15

Thr Ile Thr Leu Phe Ser Ala Asn Ile Asp Ala Ile Thr Ser Leu Ser
            20                  25                  30

Val Gly Gly Glu Leu Val Phe Gln Thr Ser Val Gln Gly Leu Val Leu
            35                  40                  45

Gly Ala Thr Ile Tyr Leu Ile Gly Phe Asp Gly Thr Thr Val Ile Thr
        50                  55                  60

Arg Ala Val Ala Ala Asp Asn Gly Leu Thr Ala Gly Thr Asp Asn Leu
65                  70                  75                  80

Met Pro Phe Asn Leu Val Ile Pro Thr Asn Glu Ile Thr Gln Pro Ile
                85                  90                  95

Thr Ser Ile Lys Leu Glu Val Val Thr Ser Lys Ser Gly Gly Gln Ala
            100                 105                 110

Gly Asp Gln Met Ser Trp Ser Ala Ser Gly Ser
        115                 120

<210> SEQ ID NO 3
<211> LENGTH: 123
<212> TYPE: PRT
<213> ORGANISM: Virus

<400> SEQUENCE: 3

Ala Ala Asp Asn Tyr Gln Phe Ser Ser Gln Tyr Gln Thr Gly Gly Val
1               5                   10                  15

Thr Ile Thr Leu Phe Ser Ala Asn Ile Asp Ala Ile Thr Ser Leu Ser
            20                  25                  30

Val Gly Gly Glu Leu Val Phe Lys Thr Ser Val Gln Ser Leu Val Leu
            35                  40                  45

Gly Ala Thr Ile Tyr Leu Ile Gly Phe Asp Gly Thr Ala Val Ile Thr
        50                  55                  60

Arg Ala Val Ala Ala Asn Asn Gly Leu Thr Ala Gly Ile Asp Asn Leu
65                  70                  75                  80

Met Pro Phe Asn Leu Val Ile Pro Thr Asn Glu Ile Thr Gln Pro Ile
                85                  90                  95

Thr Ser Ile Lys Leu Glu Ile Val Thr Ser Lys Ser Asp Gly Gln Ala
            100                 105                 110

Gly Glu Gln Met Ser Trp Ser Ala Ser Gly Ser

```
            115                 120

<210> SEQ ID NO 4
<211> LENGTH: 123
<212> TYPE: PRT
<213> ORGANISM: Virus

<400> SEQUENCE: 4

Ala Ala Asp Asn Tyr Gln Phe Ser Ser Gln Tyr Gln Thr Gly Gly Val
1               5                   10                  15

Thr Ile Thr Leu Phe Ser Ala Asn Ile Asp Ala Ile Thr Ser Leu Ser
            20                  25                  30

Val Gly Gly Glu Leu Val Phe Lys Thr Ser Ile Gln Asn Leu Val Leu
        35                  40                  45

Gly Ala Thr Ile Tyr Leu Ile Gly Phe Asp Gly Thr Ala Val Ile Thr
    50                  55                  60

Arg Ala Val Ala Ala Asn Asn Gly Leu Thr Ala Gly Ile Asp Asn Leu
65                  70                  75                  80

Met Pro Phe Asn Leu Val Ile Pro Thr Asn Glu Ile Thr Gln Pro Ile
                85                  90                  95

Thr Ser Ile Lys Leu Glu Ile Val Thr Ser Lys Ser Gly Gly Gln Ala
            100                 105                 110

Glu Asp Gln Met Ser Trp Ser Ala Ser Gly Ser
        115                 120

<210> SEQ ID NO 5
<211> LENGTH: 123
<212> TYPE: PRT
<213> ORGANISM: Virus

<400> SEQUENCE: 5

Ala Ala Asp Asp Tyr Gln Phe Ser Ser Gln Tyr Gln Thr Gly Gly Val
1               5                   10                  15

Thr Ile Thr Leu Phe Ser Ala Asn Ile Asp Ala Ile Thr Ser Leu Ser
            20                  25                  30

Val Gly Gly Glu Leu Val Phe Lys Thr Ser Val His Ser Leu Val Leu
        35                  40                  45

Gly Ala Thr Ile Tyr Leu Ile Gly Phe Asp Gly Ser Ala Val Ile Thr
    50                  55                  60

Arg Ala Val Ala Ala Asn Asn Gly Leu Thr Thr Gly Thr Asp Asn Leu
65                  70                  75                  80

Met Pro Phe Asn Leu Val Ile Pro Thr Asn Glu Ile Thr Gln Pro Ile
                85                  90                  95

Thr Ser Ile Lys Leu Glu Ile Val Thr Ser Lys Ser Gly Gly Gln Glu
            100                 105                 110

Gly Asp Gln Met Ser Trp Ser Ala Ser Gly Ser
        115                 120

<210> SEQ ID NO 6
<211> LENGTH: 123
<212> TYPE: PRT
<213> ORGANISM: Virus

<400> SEQUENCE: 6

Ala Ala Asp Asp Tyr Gln Phe Ser Ser Gln Tyr Gln Thr Gly Gly Val
1               5                   10                  15

Thr Ile Thr Leu Phe Ser Ala Asn Ile Asp Ala Ile Thr Ser Leu Ser
            20                  25                  30
```

-continued

```
Val Gly Gly Glu Leu Val Phe Lys Thr Ser Val Gln Ser Leu Val Leu
        35                  40                  45

Gly Ala Thr Ile Tyr Leu Ile Gly Phe Asp Gly Thr Ala Val Ile Thr
    50                  55                  60

Arg Ala Val Ala Ala Asn Asn Gly Leu Thr Ala Gly Ile Asp Asn Leu
65                      70                  75                  80

Met Pro Phe Asn Leu Val Ile Pro Thr Asn Glu Ile Thr Gln Pro Ile
            85                      90                  95

Thr Ser Ile Lys Leu Glu Ile Val Thr Ser Lys Ser Asp Gly Gln Ala
            100                 105                 110

Gly Asp Gln Met Ser Trp Ser Ala Ser Gly Ser
        115                 120
```

INFECTIOUS BURSAL DISEASE VIRUS ANTIGENIC ISOLATES AND VACCINES

This application is a continuation of U.S. application Ser. No. 11/811,222 filed on Jun. 8, 2007, which is a continuation of U.S. application Ser. No. 11/076,713, filed on Mar. 10, 2005, which claims the benefit under 35 U.S.C. §119(e) to U.S. Provisional Application No. 60/552,989, filed Mar. 12, 2004, each of which is hereby incorporated by reference in its entirety.

FIELD OF THE INVENTION

The present invention relates to novel antigenic isolates of Infectious Bursal Disease Virus, as well as to vaccine compositions containing one or more of these isolates. The invention also relates to new methods for preventing or ameliorating Infectious Bursal Disease in poultry.

BACKGROUND OF THE INVENTION

Infectious Bursal Disease, also called "Gumboro Disease," is an acute and highly contagious viral infection of young chickens and other fowl. It is caused by Infectious Bursal Disease Virus (IBDV) Type I, which is a member of a group of viruses called *Birnaviridae*. The disease is characterized by degeneration of lymphoid tissue. The primary target of infection is the bursa of Fabricius, although lymphoid damage may also occur in the spleen, thymus, and gland of Harder.

Degeneration of the bursa of Fabricius and other lymphoid tissue in young chickens has severe economic consequences, as the infected chickens have a decreased response to vaccination and an increased susceptibility to other infectious agents such as Newcastle disease, Marek's disease and infectious bronchitis disease. Poultry producers can lose a significant portion of their flock due to IBDV infection. Often times, mortality rates can approach 80% or more in young chickens.

Immunization is the principal method for controlling the disease. Chickens may be passively immunized, by receiving maternally-derived antibodies, or they may be actively immunized with live, live-attenuated, or killed (inactivated) vaccines. Live-attenuated vaccines contain the virus that has been "modified" or attenuated through serial passaging in cell culture. By passaging it is hoped to produce a virus strain that is less pathogenic. In order to be useful in a vaccine, however, it must retain the antigenic and immunogenic properties of the original virus. It must, that is, induce the production of neutralizing antibodies. Control of the disease by immunization had been largely successful until variant strains began to emerge as the result of antigenic drift under field conditions. These variants were causing disease in both actively and passively immunized chickens.

Infectious Bursal Disease Virus is often separately classified in the art as either Standard or "STC" strain, or variant types, although the vast majority of wild-type IBDVs in the United States are now variants. Delaware viruses are some of the most common variant types, and Delaware E in particular has been considered the prototypical variant type for years. IBDV surveys indicate that Delaware E virus is still commonly isolated; however, other variant virus types such as GLS, Rs593 and AL2 have also become quite prevalent. These strains can be characterized using a panel of monoclonal antibodies. In addition, using PCR-RFLP techniques, a distinct molecular class of viruses (called Group 6) have risen in prevalence over the past several years. Amino acid sequencing of this family of viruses shows that most are distinct from the prototype Delaware-E virus in the region generally regarded as perhaps one of the most critical to antigenic identity or uniqueness.

U.S. Pat. No. 5,919,461 relates to a live, variant vaccine strain which is reportedly effective in immunizing young chickens against the Standard, the Delaware and other new-type variant strains.

U.S. Pat. No. 6,471,962 discloses the use of certain monoclonal antibodies in the diagnosis, prevention and treatment of Infectious Bursal Disease.

U.S. Pat. No. 5,192,539 relates to an IBDV vaccine for poultry with antigen material which is derived from a mammalian cell line.

U.S. Pat. No. 5,804,195 provides a vaccine for preventing infectious bursal disease which contains specific strains of live, attenuated but intermediately virulent IBDV. The vaccine may contain other poultry immunogens, including those against Newcastle Disease virus, Marek's disease virus, and infectious bronchitis virus.

In addition, WO 9105569 is related to a diagnostic and vaccine which utilizes an IBDV variant with altered recognition sites.

There currently exists a need in the art for better antigenic isolates of IBDV, as well as vaccines which comprise these isolates for use against IBDV infection. Also needed are better methods of protecting poultry, in particular chickens, from the many variants of the IBD virus, including newer ones that have recently emerged.

SUMMARY OF THE INVENTION

Figure 1:
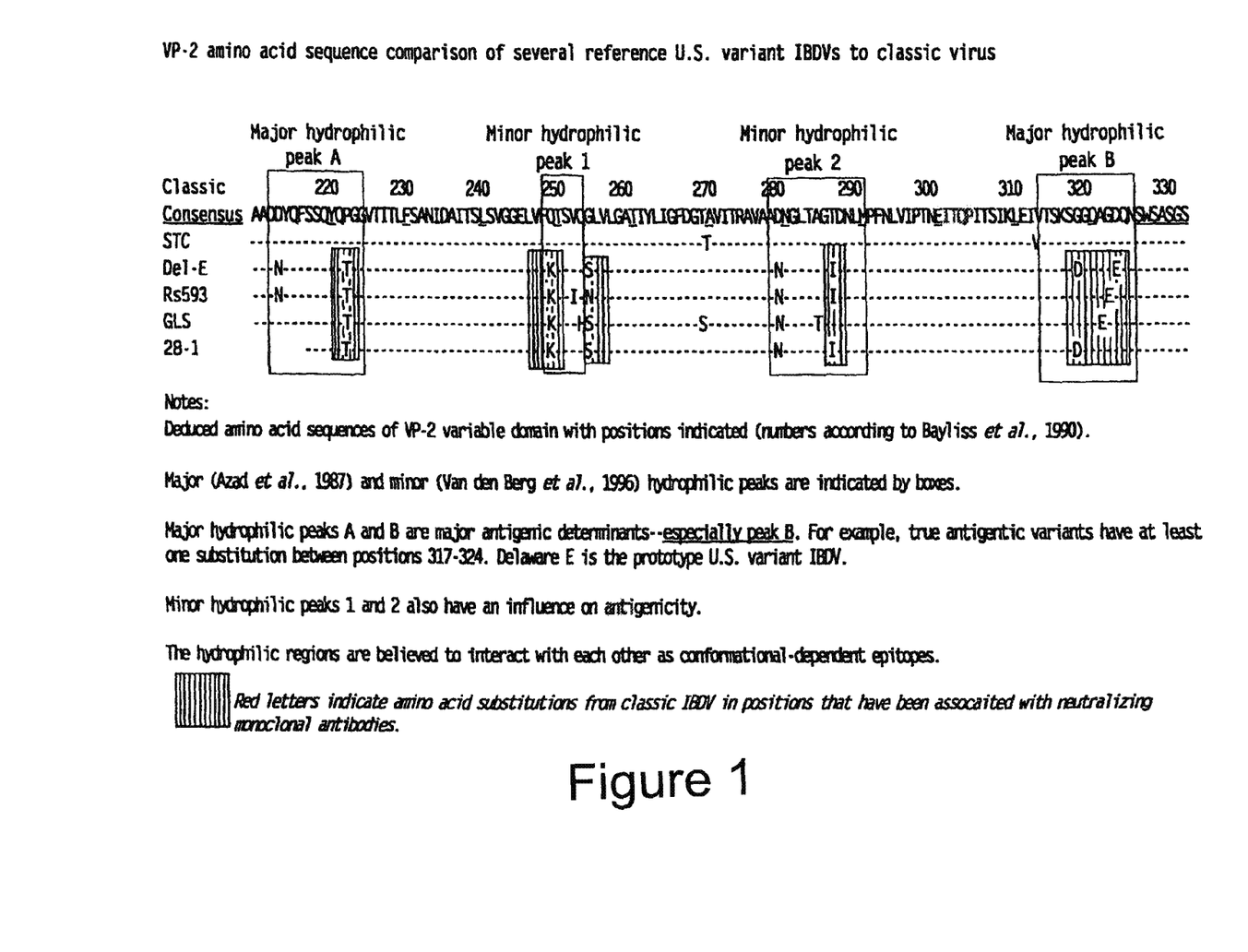
FIG. 1 is an amino acid sequence comparison of several reference U.S. variant IBDVs to classic (standard) virus. The "Consensus" sequence shown in FIG. 1 is represented by SEQ ID NO:1, and the VP-2 variable domains of STC, Del-E, Rs593, GLS and 28-1 are represented by SEQ ID NOs: 2 through 6, respectively.

In one aspect, the invention is directed to a vaccine composition which is effective in preventing or ameliorating Infectious Bursal Disease Virus infection, which comprises an antigen or antigenic component having the substantive identifying characteristics of an Infectious Bursal Disease Virus antigen as set forth in FIG. 1. As that term is used herein, "substantive identifying characteristics" means the amino acid sequence of isolate 28-1 in FIG. 1, which comprises only one substitution G->D at position 318, i.e. 318-D, in major hydrophilic peak B of the Viral Protein-2 (VP-2) of IBDV, and in addition, one or more of the other substitutions noted for isolate 28-1 in FIG. 1, including the following: 222-T, 249-K, 254-S or N, 279-N and 286-I. In addition, the antigen or antigenic component should retain substantial reactivity with a basic panel of monoclonal antibodies that characterizes Delaware strain variant viruses.

Thus, the invention provides a vaccine composition comprising an antigen or antigenic component having a 318-D as the only substitution in major hydrophilic peak B of the VP-2 amino acid sequence of Infectious Bursal Disease Virus.

The invention is also directed to a vaccine composition against Infectious Bursal Disease Virus, which comprises the novel 28-1 antigenic isolate of IBDV deposited on Mar. 4, 2004 with the ATCC under Accession Number PTA-5848.

In a further embodiment of the invention there is provided an Infectious Bursal Disease Virus antigenic isolate having a 318-D as the only substitution in major hydrophilic peak B of the VP-2 amino acid sequence which is suitable for use in a vaccine against IBD.

The invention also provides an Infectious Bursal Disease Virus antigenic isolate having the amino acid sequence set forth in FIG. 1 (28-1). This is a unique isolate in what is now referred to as the molecular Group 6 family of IBDV isolates.

In addition, there is provided an Infectious Bursal Disease Virus antigenic isolate deposited on Mar. 4, 2004 with the ATCC under Accession Number PTA-5848 as part of the invention.

Also provided is a method for inducing protection against infection from Infectious Bursal Disease Virus, which involves administering to a poultry animal a vaccine composition containing an antigen having the substantive identifying characteristics of an IBDV antigenic isolate as set forth in FIG. 1.

The invention further provides a method for inducing protection against Infectious Bursal Disease, which comprises administering to a poultry animal an antigenic isolate identified with ATCC Accession # PTA-5848.

These and other embodiments, features and advantages of the invention will become apparent from the detailed description and the appended claims set forth herein below.

DETAILED DESCRIPTION OF THE INVENTION

In one aspect, the present invention is directed to a novel Infectious Bursal Disease Virus (IBDV) antigenic isolate. The isolate is generally characterized as a Delaware-type virus using monoclonal antibody-antigen-capture ELISA, in that it reacts the same as Delaware-E against a limited panel of monoclonal antibodies. In addition, the virus is further characterized using the reverse transcriptase-polymerase chain reaction/restriction fragment length polymorphism (RT-PCR/RFLP) method of Jackwood et al., *Restriction Fragment Length Polymorphisms in the VP2 Gene of Infectious Bursal Disease Viruses*, Avian Dis. 41:627-637, 1997, as a molecular Group 6 virus (rather than molecular Group 2 to which the prototype Delaware-E variant is assigned).

Referring to FIG. 1, further characterization in terms of the amino acid sequence of the variable region of the major antigenic Viral Protein 2 (VP-2) is set forth, along with sequence information from established isolates for comparison. Also included is a summary of the characterization of IBDV isolates with particular attention to the special qualities of the 28-1 isolate as a suitable example (hereinbelow defined). Those skilled in the art will recognize that VP-2 is one of the two major structural proteins of IBDV and is also the target of the serotype-specific neutralizing antibodies which confer protective immunity. (The second major structural protein of the virus, VP-3, does not elicit neutralizing antibodies.)

As FIG. 1 illustrates, IBDV isolates have two major and two minor hydrophilic peak regions. Without being bound by theory, all the hydrophilic regions, and in particular the major hydrophilic regions, are believed to have an important effect on antigenicity. The 28-1 isolate has 318-D as its sole substitution in peak B noted in FIG. 1, and is thus separately identifiable from other reference IBDV variants, including the classic (standard—STC) strain and the Delaware-E strain. In fact, the 28-1 isolate differs from Delaware-E in what is generally regarded as the most critical antigenic region of IBDV—major hydrophilic peak B. In addition, the 28-1 isolate of IBDV has one or more of the following additional substitutions: 222-T, 249-K, 254-S or N, 279-N and 286-I (as per commonly accepted single letter amino acid abbreviations). In addition, the 28-1 isolate differs from the Delaware-A variant at position 222. Delaware-A has 222-Q which is a relatively rare substitution in this position, whereas the 28-1 has 222-T in its preferred embodiment. Most field viruses have 222-T, which perhaps indicates that the 28-1 isolate is a better antigenic match than Delaware-A for U.S. field viruses, and also significant enough to distinguish the two strains as well. A summary of the amino acid patterns in the virus strains presented in FIG. 1 is set forth in TABLE 1 below:

TABLE 1

COMPARISON OF REFERENCE VIRUS AMINO ACID PATTERNS IN CRITICAL VP-2 POSITIONS.

| Virus | 222 | 249 | 254 | 286 | 318 | 321 | 322 | 323 |
|---|---|---|---|---|---|---|---|---|
| Classic-STC | P | Q | G | T | G | A | G | D |
| Delaware E | T | K | S | I | D | A | G | E |
| GLS | T | K | S | T | G | E | G | D |
| Rs593 | T | K | N | I | G | A | E | D |
| 28-1 | T | K | S | I | D | A | G | D |
| Delaware A | Q | K | S | I | D | A | G | D |

Positions 318, 321, 322 and 323 are located in Peak B and amino acid changes result in antigenic change.

Each of the positions above in TABLE 1 has been linked to the binding of neutralizing monoclonal antibodies, and thus the skilled artisan can see the differences between the strains, including the Group 6 28-1 isolate.

Figure 2:
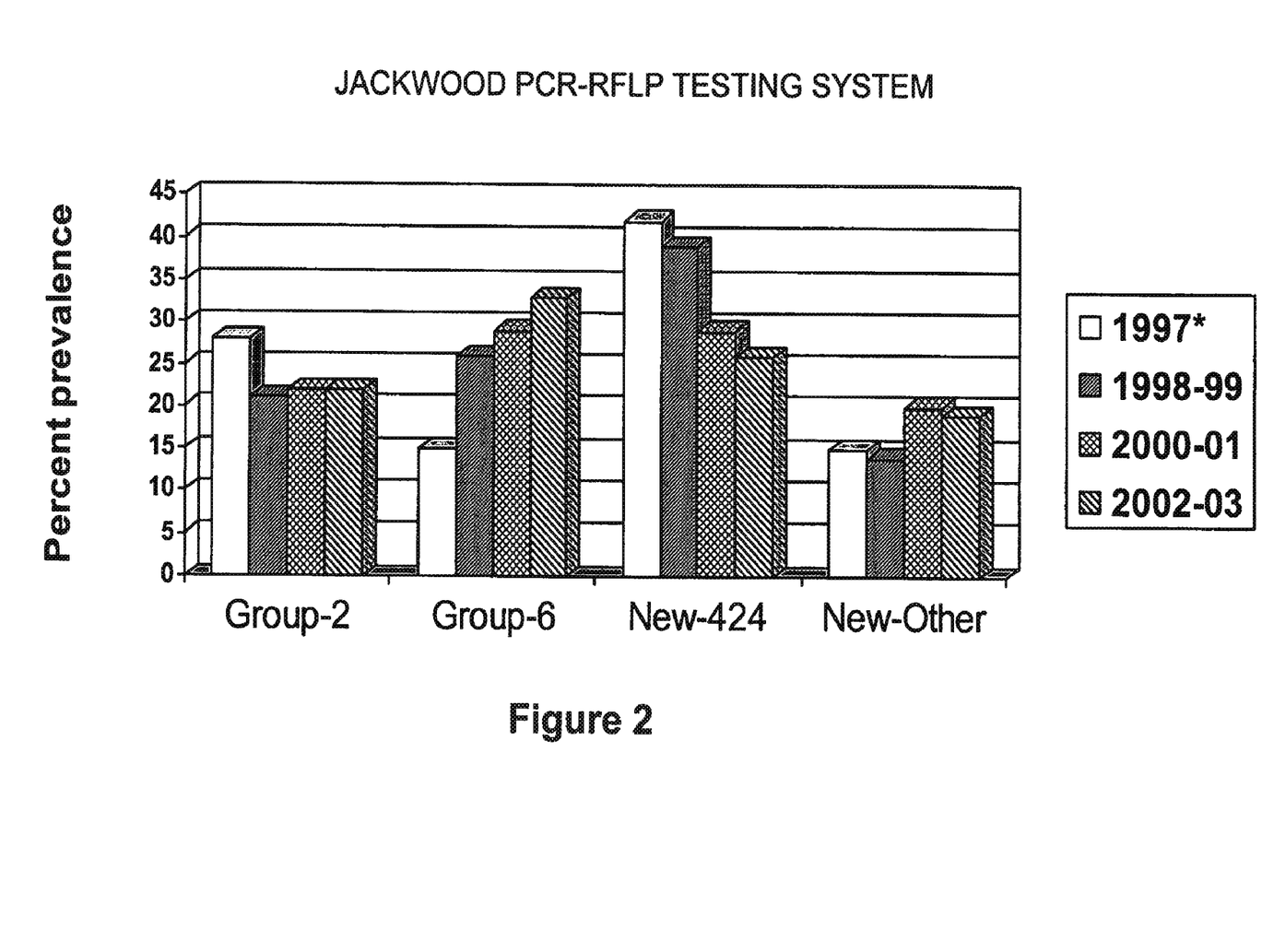
FIG. 2 depicts the Jackwood PCR-RFLP testing system showing the prevalence of wild-type viruses in the United States over time. 1997 data is taken from Jackwood survey. 1998-2003 data is taken from Fort Dodge surveys of over 600 positive samples.

Accumulation of data via PCR typing of U.S. field samples has now clearly shown the prevalence and significance of the molecular Group 6 IBDV viruses. Group 6 viruses are by far the most common molecular type recovered from U.S. broilers, accounting for approximately 1 in 3 field isolates, as FIG. 2 indicates. Without being bound by any theory, the increasing prevalence of Group 6 viruses in U.S. broilers since 1997 is likely a result of more successful escape from Delaware-E and Classic type antibodies provided by conventional IBD vaccines. In support of this concept is the fact that sequencing analysis of several U.S. field samples shows that most IBD viruses in the Group 6 family do not have the Delaware-E substitution pattern in the major hydrophilic Peak B—Jackwood et al., *Amino Acid Comparison of Infectious Bursal Disease Viruses Placed in the Same and Different Molecular Groups by RT/PCR-RFLP*, Avian Dis. 45:330-339, 2001.

The practical significance of the Group 6 family of viruses was recently explored by conducting a progeny challenge study of five breeder flocks on five different killed IBD vaccination programs. One of Jackwood's Group 6 variants was compared against Delaware E and GLS strain viruses in a progeny challenge study. Results showed that the Group 6 variant virus broke through maternal antibodies at a higher rate than did either of the Delaware E and GLS strain variants, resulting in more bursal atrophy and fewer protected birds.

This study demonstrated that only the threat posed by wild virulent Group 6 viruses, but also further reinforced the need for an effective vaccine against it.

One Group 6 IBDV isolate that is especially preferred for use in the present invention has now been identified as isolate 28-1. Isolate 28-1 has substitution 318-D noted in FIG. 1, and in addition, has one or more of the following additional substitutions in VP-2 of IBDV: 222-T, 249-K, 254-S or N, 279-N and 286-I. Preferably, the 28-1 isolate will have at least two of the additional substitutions noted, in particular 222-T and 254-S or N, and more preferably at least three, four, or all five of the additional substitutions noted. A suitable example has been deposited with the ATCC under Accession Number PTA-5848 on Mar. 4, 2004. The virus isolate 28-1 differs from previous isolates by a combination of its molecular group classification (as set forth above), and also by the fact that it retains substantial reactivity with the basic panel of monoclonal antibodies that characterize the Delaware type variant viruses.

The Group 6 IBDV antigenic isolates, and in particular the 28-1 isolate, may be isolated using techniques available in the art. For example, bursae from infected chickens may be obtained from a commercial broiler flock. The virus may then be passaged in bursal tissue or other suitable media to establish a master seed virus. Further characterization by the skilled artisan may also be undertaken using available methods.

In a further aspect herein, the invention also comprises a vaccine composition containing one or more of the Group 6 IBDV antigenic isolates described. It is especially preferred that the IBDV antigenic isolate demonstrate significant immunogenic and safety characteristics when formulated into a vaccine composition. It is highly preferred that the qualities of the vaccine composition be sufficient to obtain regulatory approval and licensure thereof from the USDA. The 28-1 isolate, and other isolates having substantially the same substantive identifying characteristics, are highly preferred for the vaccine composition. The Group 6 antigenic isolates herein described should offer significant cross-protection against a wide range of IBDV challenge variants, including without limitation, the Standard (STC), as well as the Delaware and AL-2 variants, and variants from the Group 6 molecular family, including 28-1. Protection against the Shelton 21, or S-21 variant strain of the Group 6 family is also contemplated herein—the S-21 variant has the following substitutions in the VP-2 region: 318-N and 321-E.

The vaccine composition of the invention may be formulated using available techniques, preferably with a pharmacologically acceptable carrier. For example, in one embodiment an aqueous formulation is contemplated. Such formulations utilize water, saline, or phosphate or other suitable buffers. In still another embodiment, the vaccine composition is preferably a water-in-oil or oil-in-water emulsion. Also contemplated are double emulsions, often characterized as water-in-oil-in-water emulsions. The oil may help to stabilize the formulation and further function as a vaccine adjuvant. Suitable oils may be selected by the skilled artisan, and can include, without limitation, white oil, Drake oil, squalane or squalene, as well as other animal, vegetable or mineral oils, whether naturally-derived or synthetic in origin. In addition, the vaccine composition may contain other suitable adjuvants available in the art. These can include aluminum hydroxide and aluminum phosphate, for example, as well as other metal salts.

Additional excipients may also be included in the vaccine composition, such as surfactants or other wetting agents. Surfactants can include the sorbitan mono-oleate esters (TWEEN® series), as well as the ethylene oxide/propylene oxide block copolymers (PLURONIC® series), as well as others available in the art. Other compounds recognized as stabilizers or preservatives may also be included in the vaccine. These compounds include, without limitation, carbohydrates such as sorbitol, mannitol, starch, sucrose, dextrin or glucose and the like, as well the preservative formalin, for example.

The vaccine composition may also be formulated as a dry powder, substantially free of exogenous water, which may then be reconstituted by an end user.

The vaccine composition may contain live virus, or live, but attenuated virus. Also contemplated is killed or inactivated virus for use in the invention. In one embodiment, the virus utilized in the vaccine composition has been attenuated using serial passaging techniques. Whole or partial antigenic isolate may be utilized. It is highly preferred that whatever form of antigenic isolate is selected, the identifying characteristics of the Group 6 family, in particular the antigenic features hereinabove described, be retained in the featured vaccine virus. Also contemplated for use herein is a recombinant vaccine, which expresses the nucleic acids, amino acid sequence, and/or proteins having the identifying structural characteristics of the Group 6, e.g. 28-1, antigenic isolates herein described.

The vaccine composition of the invention will contain an effective amount of IBD virus isolate for preventing or ameliorating Infectious Bursal Disease. In one embodiment of the invention, the vaccine will contain from about $10^{2.0}$ to about $10^{6.0}$ $EID_{50}$ ("Egg Infectious Dose") of isolate per dose. A dose is typically within the range of about 0.25 mL to about 2.0 mL per poultry animal, more preferably about 0.5 mL to about 1.0 mL per animal.

The vaccine composition herein described may be administered with the novel antigenic isolate set forth above, and in addition, may also contain one or more other IBDV variants as vaccine antigens, in particular, those that are recognized as being efficacious against the disease. For example, the Lukert strain, first isolated by Dr. Phil Lukert of the University of Georgia at Athens and developed by Salsbury Laboratories, Inc., may be co-administered in an IBDV vaccine composition.

Other poultry antigens against other diseases may also be included and administered with the vaccine composition of the invention. For example, vaccine antigens against chicken herpes virus, chicken anemia virus (CAV), Newcastle Disease virus and Infectious Bronchitis (IB) virus, as well as reovirus antigens may be included as part of the vaccine composition of the invention. One or more reovirus antigens may be particularly preferred as part of the vaccine composition of the invention.

The invention is also directed to a method for inducing protection against infection from Infectious Bursal Disease Virus. The method involves administering to a poultry animal a vaccine composition containing an antigen having the substantive identifying amino acid characteristics of an IBDV antigenic isolate as set forth in FIG. 1, i.e. an isolate from the now-identified family of Group 6 variants. In particular, the isolate 28-1 is preferred, and the isolate as set forth above which is deposited under ATCC Accession # PTA-5848 on Mar. 4, 2004 is particularly desirable.

The method of administration may be selected by the skilled artisan. In ovo administration is contemplated herein. For example, embryos may be inoculated, usually at about day 18-19. In addition, the vaccine composition may be administered to post-hatch, young (few days to several weeks old) chicks via drinking water, spraying or eye drops. Other methods wherein the vaccine composition of the invention is administered parenterally, subcutaneously, peritoneally, orally, intranasally, or by other available means, preferably parenterally, more preferably intramuscularly, in effective amounts according to a schedule which may be determined according to the time of anticipated potential exposure to a carrier of the disease-causing Infectious Bursal Disease Virus, are also within the scope of the invention.

As set forth above, the invention is directed to novel IBDV antigenic isolates, vaccine compositions and methods for poultry. The term "poultry" is intended to encompass, without limitation, all commercially-bred poultry animals, including chickens, ducks, geese, peafowl, bantam fowl, and the like.

In a further embodiment of the invention, there is also provided a marker vaccine for IBDV which utilizes the antigenic isolate as set forth in FIG. 1 (28-1) to distinguish between vaccinated and unvaccinated members of a flock, as well to distinguish vaccinated animals from those that may have been infected with one or more other variants of the virus. The marker vaccine may also include a reagent kit for testing animals. The reagent kit could include more or one antigenic isolates, such as 28-1, as well as antibodies which recognize and react therewith.

EXAMPLES

The following examples illustrate various preferred aspects of the invention, but should not be construed as in any way limiting the full scope thereof.

Example 1

Study Summary

Specific Pathogen Free (SPF) White Leghorn chickens were vaccinated at five weeks of age with $\frac{1}{50}^{th}$ of a dose of prototype, inactivated, Infectious Bursal Disease Virus (IBDV)/Avian Reovirus combination vaccines. The vaccines contained Avian Reovirus antigens and Infectious Bursal Disease virus, Lukert strain, with or without the addition of the variant IBDV strains of bursal tissue origin (BTO). Test vaccines were formulated into a 55% oil:45% aqueous ratio, 0.5 mL format. A competitor IBDV/Reo vaccine product was also administered at $\frac{1}{50}^{th}$ of a dose to a group of chickens.

The groups were bled for serum at 24 days post-vaccination and were challenged with variant S-21, Delaware variant E or variant AL2 IBDV isolates at 28 days post-vaccination. Bursa to body weight ratios were recorded at 10 days post-challenge.

Serologic and protection data from vaccinated chickens indicated that the antigen prepared from a variant isolate designated 28-1, and in particular when added to IBDV Lukert ACL in an inactivated vaccine, significantly increased immunogenicity.

It was concluded that further vaccine development efforts should include the 28-1 variant strain IBDV antigen.

Evaluation of Additional Variant IBDV Isolates as Inactivated Vaccines

Fractional Dose Study

Background

A number of field isolates of Infectious Bursal Disease Virus (IBDV) were accessioned from cases in which a molecular typing system revealed novel or unique patterns to indicate viruses of variant antigenicity. This example was undertaken to examine and characterize a number of these isolates further for possible future development as either live, live (attenuated), or inactivated vaccines. The first step in the characterization was to evaluate the pathogenicity of the viruses. Based on the results of the initial trial, selected isolates were used as challenge viruses to determine which, if any, had the capability to break through immunity induced by current inactivated vaccines. The third study attempted to evaluate the use of two identified variant isolates in combination with IBDV Lukert ACL in inactivated vaccines, but it was invalidated by inadvertent pre-challenge virus exposure.

The currently described study was designed to evaluate the use of BTO antigens from alternate variant IBDV isolates in combination with IBDV Lukert ACL in inactivated vaccines. Serologic response, as measured by ELISA and serum neutralization (SN) assays, and protection against three variant challenge strains were assessed.

Objective(s)

Compare the ability of prototype vaccines, prepared to include BTO antigen from IBDV variant isolates S-21, 15-4 (a Delaware strain variant), 28-1 and ArkProvent, to immunize chickens. (S-21 and ArkProvent are other molecular Group 6 virus isolates, but S-21 is considered a novel type as defined by a panel of monoclonal antibodies, and ArkProvent has not been so defined).

Evaluate the performance of the prototype vaccines in comparison to a competitor product.

Materials and Methods

Event Log

| Test Day | Activity |
|---|---|
| 0 | Vaccinated appropriate groups at 4 weeks of age |
| 24 | Bled 15 birds per vaccine group and 20 birds from the nonvaccinated groups. |
| 28 | Challenged appropriate groups with IBDV challenge isolates |
| 38 | Determined bursa to body weight ratios. |

Animal Selection

Test Animals
Type: *Gallus domesticus*
Number: 400 (375 used in testing and 25 extras)
Serological Status: SPF
Age/Weight range: 3 weeks of age
Sex: Mixed
Breed: White Leghorn
Identification: Isolator cage cards
Source: HyVac
Preadmission/exclusion criteria: Only chickens in an apparently healthy condition at the time of inoculation were used. Any chicks which by their behavior or appearance were deemed to be in an ill-thriven state were excluded from the study.

Housing and Care of Animals

The chickens were housed in negative pressure, modified Horsfal type Plexiglas isolators in the appropriate building of the test facility. They were provided feed and water ad libitum for the duration of the study. Standard poultry care procedures for the animal testing facility were used.

Test Vaccines

Composition of Vaccine

A total of seven vaccines were tested in the study. One vaccine was an actual competitor's product (which contains at least one BTO antigen component) and the remaining six vaccines were prepared by Research & Development at Fort Dodge Animal Health, Fort Dodge, Iowa.

Test vaccines were comprised of inactivated IBDV and avian reovirus viral fluids formulated into a water-in-oil emulsion. IBDV Lukert ACL lot antigen was sourced from the Bioproduction facility, and was added to five of the vaccines in an amount to yield a relative potency (RP) of 1.0 as compared to the stock antigen. The Shelton 21, 15-4, 28-1 and ArkProvent variant fluids were sourced from bursal tissue prepared in Research & Development, and were added in an amount to yield a dose of $10^{4.0}$ $EID_{50}$ per 0.5 ml. The fifth vaccine contained only the base IBDV Lukert ACL antigen with no variant.

IBDV Lukert of chicklet origin, lot #XXXX-XX-XX was added to the sixth vaccine to yield $10^{6.5}$ $TCID_{50}$ per 0.5 mL dose. Additionally, the Shelton 21 antigen was added at $10^{4.0}$ $EID_{50}$ per 0.5 mL.

Avian Reovirus antigens were sourced from TTPI-produced, ACL propagated stocks and were added to all vaccines to yield $10^{6.7}$ $TCID_{50}$ per 0.5 mL dose. The formulations were 55% oil:45% aqueous ratio with Arlacel 83 and Tween 80 as emulsifiers, formulated for the 0.5 mL final volume per dose.

Source of Vaccine

Vaccines were prepared in the Fort Dodge R&D facility with the exception of the competitor's product which was obtained from a commercial distributor.

Shipment of Vaccine

Vaccines were shipped prior to the initiation of the study on the regular intra-facility shuttle, and were transported and stored to maintain a temperature of 2° C. to 7° C.

Serial Number

Prototype Fort Dodge vaccines were not identified by serial number. The individual bottles were labeled with the name indicated in the table of Treatments below (TABLE 3).

Competitor's product—serial #1159011 (also contained reovirus antigen)

Quality Control Testing or EU Batch Certificate (if Available)

No testing was performed on the vaccines by the Quality Control Department. Fort Dodge R&D performed pre-inactivation titration and completeness of inactivation testing on the variant BTO antigens as a basis for developing vaccine formulations.

Storage

Vaccines were stored at 2° C. to 7° C.

TABLE 3

EXPERIMENTAL DESIGN

| Group | Treatment | Route/Volume | Challenge | # birds |
|---|---|---|---|---|
| A | Chicklet Lukert + S21 | IM/0.01 mL | See Challenge Procedure below | 45 |
| B | Lukert ACL only | IM/0.01 mL | See below | 45 |
| C | Lukert ACL + S21 | IM/0.01 mL | See below | 45 |
| D | Lukert ACL + 28-1 | IM/0.01 mL | See below | 45 |
| E | Lukert ACL + 15-4 | IM/0.01 mL | See below | 45 |
| F | Lukert ACL + ArkProvent | IM/0.01 mL | See below | 45 |
| H | Competitor's product | IM/0.01 mL | See below | 45 |
| I | Challenge control | N/a | See below | 45 |
| J | Normal control | N/a | n/a | 15 |

Vaccination

Chickens were vaccinated once, intramuscularly, in the breast. The vaccine was delivered using a microsyringe with mechanical repeating apparatus fitted to a 20 gauge needle, and 0.010 mL volume was administered to each chicken at 5 weeks of age.

Challenge and Observation Procedure

Appropriate dilutions of the Shelton 21, Delaware variant E and AL2 challenge isolates were made in sterile tryptose phosphate broth to achieve a dose of $10^{3.0}$ to $10^{3.5}$ $EID_{50}$ per chicken. The challenge was administered by eye drop, using a pipettor and delivering 30 µl to one eye of each of 15 birds per group for each isolate. Challenge took place at four weeks post-vaccination.

At ten days post challenge, the groups were euthanized and bursa to body weight ratios were determined.

Challenge table:

| Challenge isolate | Dose/Administration | Challenge scheme |
|---|---|---|
| Shelton 21 | $10^{3.5}$ $EID_{50}$ per 0.03 mL eyedrop to 15 birds/group | Once at 28 days post-vaccination |
| Variant E | $10^{3.5}$ $EID_{50}$ per 0.03 mL eyedrop to 15 birds/group | Once at 28 days post-vaccination |
| AL2 | $10^{3.5}$ $EID_{50}$ per 0.03 mL eyedrop to 15 birds/group | Once at 28 days post-vaccination |

Sample Collection and Testing

Blood samples were collected at 24 days post-vaccination. The blood was allowed to coagulate and the serum was decanted into separate tubes. The sera was frozen and sent to Fort Dodge R&D for serologic analysis by Idexx ELISA (extended range) and in-house virus neutralization assays.

To determine bursa to body weight (B/BW) ratios, the chickens were euthanized and the body weight of each bird was recorded. For each bird, the bursa was excised in its entirety and was similarly weighed.

Samples of the bursae were also collected in neutral buffered formalin and archived.

Data Analysis

Geometric mean IBDV ELISA titers for the groups were calculated and compared by one way ANOVA and Fisher's PLSD ($\alpha=0.05$) after importation of the data into the Statview software package. ELISA data was also evaluated in terms of percent positive, wherein any sample with a signal to positive control (S/P) ratio greater than 0.20 was considered antibody positive. (as specified by the ELISA assay kit manufacturer, Idexx). For serum neutralization data, geometric mean titers were also calculated, and for defining percent positive, any sample with a reciprocal dilution of 20 or greater was considered antibody positive.

The B/BW ratio was calculated by dividing a recorded bursa weight by its associated body weight and multiplying by 1000. The normal controls were used to establish a mean normal B/BW ratio, and a cutoff value was calculated to be two standard deviations less than this mean. Any bird with a B/BW ratio less than the cutoff value was considered affected by challenge, thus not protected by vaccination. This analysis yielded data of percent protected.

Group mean B/BW ratios were also compared by one way ANOVA ($\alpha$=0.05) and Fisher's PLSD after importation of the data into the software package. A group mean B/BW ratio that was significantly higher than the challenge controls indicated protection was achieved in a group. A statistically higher group mean B/BW ratio in one group compared to another group, indicated a significantly higher level of protection in that group.

Results and Discussion

Serology

ELISA and serum neutralization assay data is reported in Table 4.

The challenge control and normal control groups remained free of IBDV antibody prior to challenge, validating the biosecurity of the study.

The vaccines containing Lukert ACL with the addition of BTO-sourced variant antigen elicited significantly higher ELISA GMT against IBDV than did the Lukert ACL only group, but those titers were not always significantly higher than the nonvaccinated control groups. The Lukert ACL+15-4 vaccine elicited a significantly higher ELISA GMT than both the control and Lukert ACL only groups, but only the 28-1 antigen increased the ELISA response at or above the level of the "benchmark" competitor product.

Serum neutralization (SN) assay GMT's were low in general and thus were not evaluated statistically. In terms of percent SN positive, results similar to those obtained by ELISA were observed. The control groups were free of detectable antibody. The Lukert ACL only, Chicklet Lukert+S21, Lukert ACL+ArkProvent and Lukert ACL+S21 groups had only 1 or 2 positives, and the Lukert ACL+15-4 and Lukert ACL+28-1 groups had 5 positives.

Challenge Protection

Challenge protection was evaluated in two ways. First, as reported in Table 5, was by comparing group mean B/BW ratios. Table 5 includes comparisons split out by challenge isolate and for all challenges combined.

It is the "all challenges combined" data which may be most pertinent in evaluating the immunogenicity of the vaccines. This would be expected to provide an overall view of protection against variants in general, including more recent isolates, which is the targeted objective of any vaccine under development.

When the combined challenges data is considered, the mean B/BW ratios of Lukert ACL only, Chicklet Lukert+S21, Lukert ACL+S21 and Lukert ACL+ArkProvent groups were statistically equivalent to the challenge control group. This indicated that there was essentially no protection afforded by vaccination with $\frac{1}{50}^{th}$ of a dose of these vaccines. The Lukert ACL+15-4 group had a mean B/BW ratio that was significantly higher than the challenge control group, indicating some level of protection was induced by this vaccine. The Lukert ACL+28-1 group had a mean B/BW ratio that was significantly higher than the Lukert ACL+15-4 group, indicating a still higher level of protection. The Competitor's product vaccine fell between the Lukert ACL+15-4 and Lukert ACL+28-1 groups, and was not significantly different than either of those groups.

The data was also evaluated in terms of percent protection as derived from a cutoff value calculated from the nonchallenged, normal control group of chickens, which is reported in Table 6. Again, the data derived by combining all of the challenges is probably most pertinent. This evaluation essentially gave the same results as the group mean B/BW data (Table 5) in that the Lukert ACL+28-1 and the competitor's product vaccine elicited higher levels of protection than the others, with the Lukert ACL+28-1 group giving the numerically highest level of protection.

Discussion

One of the primary objectives of the study was to determine if other variant isolates combined with IBDV Lukert ACL would yield more antigenic vaccines as determined by serologic and protective responses. That objective was essentially achieved in the study as it was determined that supplementation of vaccine with antigen derived from the 28-1 isolate resulted in more immunogenic vaccines. When formulated into prototype vaccines at equivalent dose and administered in equivalent fractional dose volumes by equivalent routes, the 28-1 supplemented vaccines elicited significantly greater ELISA and protective responses than other vaccines.

The second objective of the study was to evaluate the various prototype vaccines in comparison to a competitor product which performed well in previous studies. By all means of evaluation except percent SN response, the vaccine supplemented with 28-1 BTO antigen met or exceeded the performance level of the competitor's product vaccine. Hence the 28-1 antigen is highly suitable for further vaccine development.

The $\frac{1}{50}^{th}$ of a normal dose given in this study was designed to give lowered protection levels such that differences between the vaccines could be elucidated.

Conclusions

The inclusion of 28-1 isolate BTO antigens significantly increased serologic and protective responses elicited by prototype vaccines.

The inclusion of 28-1 isolate BTO antigen yielded a prototype vaccine which performed at, or surpassed the level of the competitor's product when serologic response and protective response against variant IBDV was considered.

TABLE 4

SEROLOGIC RESPONSE INDUCED BY PROTOTYPE AND CURRENTLY-LICENSED INACTIVATED VACCINES WITH AN IBDV COMPONENT.

| | ELISA response | | SN response | |
|---|---|---|---|---|
| Treatment | Geometric mean titer* | % positive | Geometric mean titer | % positive |
| Chicklet Lukert + S21 | $15^{a,b}$ | 0% (0/15) | 1 | 7% (1/15) |
| Lukert ACL only | $5^a$ | 7% (1/15) | 1 | 13% (2/15) |
| Lukert ACL + S21 | $32^b$ | 0% (0/15) | 2 | 13% (2/15) |
| Lukert ACL + 28-1 | $589^d$ | 60% (9/15) | 4 | 33% (5/15) |
| Lukert ACL + 15-4 | $66^c$ | 20% (3/15) | 4 | 33% (5/15) |
| Lukert ACL + ArkProvent | $32^b$ | 20% (3/15) | 1 | 7% (1/15) |
| Competitor | $491^d$ | 73% (11/15) | 23 | 73% (11/15) |
| Challenge control | $27^b$ | 0% (0/15) | 1 | 0% (0/15) |
| Normal control | $10^{a,b,c}$ | 0% (0/5) | 1 | 0% (0/5) |

TABLE 4-continued

SEROLOGIC RESPONSE INDUCED BY PROTOTYPE
AND CURRENTLY-LICENSED INACTIVATED
VACCINES WITH AN IBDV COMPONENT.

|  | ELISA response | | SN response | |
|---|---|---|---|---|
| Treatment | Geometric mean titer* | % positive | Geometric mean titer | % positive |

*Means with the same superscripts are statistically equivalent by one-way ANOVA and Fisher's PLSD ($\alpha = 0.05$)

TABLE 5

PROTECTION AGAINST VARIANT IBDV CHALLENGE INDUCED
BY PROTOTYPE AND CURRENTLY-LICENSED INACTIVATED
VACCINES WITH AN IBDV COMPONENT AS MEASURED BY
GROUP MEAN BURSA TO BODY WEIGHT RATIOS.

|  | Mean group B/BW ratio* | | | |
|---|---|---|---|---|
|  | Challenge strain | | | All challenges |
| Treatment | S-21 | Variant E | AL-2 | combined |
| Chicklet Lukert + S21 | $0.92^a$ | $1.11^a$ | $0.97^{a,b}$ | $1.00^a$ |
| Lukert ACL only | $0.96^a$ | $1.16^{a,b,c}$ | $0.96^a$ | $1.03^a$ |
| Lukert ACL + S21 | $1.06^{a,b}$ | $0.98^a$ | $1.02^{a,b}$ | $1.02^a$ |
| Lukert ACL + 28-1 | $1.17^{a,b,c}$ | $2.24^d$ | $1.77^c$ | $1.73^c$ |
| Lukert ACL + 15-4 | $1.40^{b,c}$ | $1.52^{b,c}$ | $1.04^{a,b}$ | $1.32^b$ |
| Lukert ACL + ArkProvent | $1.01^{a,b}$ | $1.03^a$ | $0.88^a$ | $0.97^a$ |
| Competitor | $1.49^c$ | $1.62^{b,c}$ | $1.44^{b,c}$ | $1.52^{b,c}$ |
| Challenge control | $0.90^a$ | $0.99^a$ | $1.01^{a,b}$ | $0.97^a$ |
| Normal control | $4.17^d$ | $4.17^e$ | $4.17^d$ | $4.17^d$ |

*Means within columns with the same superscripts are statistically equivalent by one-way ANOVA and Fisher's PLSD ($\alpha = 0.05$)

TABLE 6

PROTECTION AGAINST VARIANT IBDV CHALLENGE
INDUCED BY PROTOTYPE AND CURRENTLY-LICENSED
INACTIVATED VACCINES WITH AN IBDV COMPONENT
AS MEASURED BY PERCENT PROTECTION IN REFERENCE
TO A CALCULATED CUTOFF VALUE.

|  | Percent Protected* | | | |
|---|---|---|---|---|
|  | Challenge strain | | | All challenges |
| Treatment | S-21 | Variant E | AL-2 | combined |
| Chicklet Lukert + S21 | 0 | 0 | 0 | 0 |
| Lukert ACL only | 0 | 7 | 0 | 2 |
| Lukert ACL + S21 | 7 | 7 | 0 | 4 |
| Lukert ACL + 28-1 | 7 | 60 | 27 | 31 |
| Lukert ACL + 15-4 | 13 | 13 | 0 | 9 |
| Lukert ACL + ArkProvent | 7 | 7 | 0 | 4 |
| Competitor | 20 | 13 | 13 | 16 |
| Challenge control | 0 | 0 | 0 | 0 |
| Normal control | n/a | n/a | n/a | 100 |

*Percent protected was based on a cutoff value using the normal control group. Normal control group mean bursa to body weight ratio (4.17) minus two standard deviations (2.23) = calculated cutoff (1.94). A bird whose bursa to body weight ratio exceeded 1.94, when necropsied 10 days post-challenge, was classified as protected.

Examples 2 and 3

Figure 3:
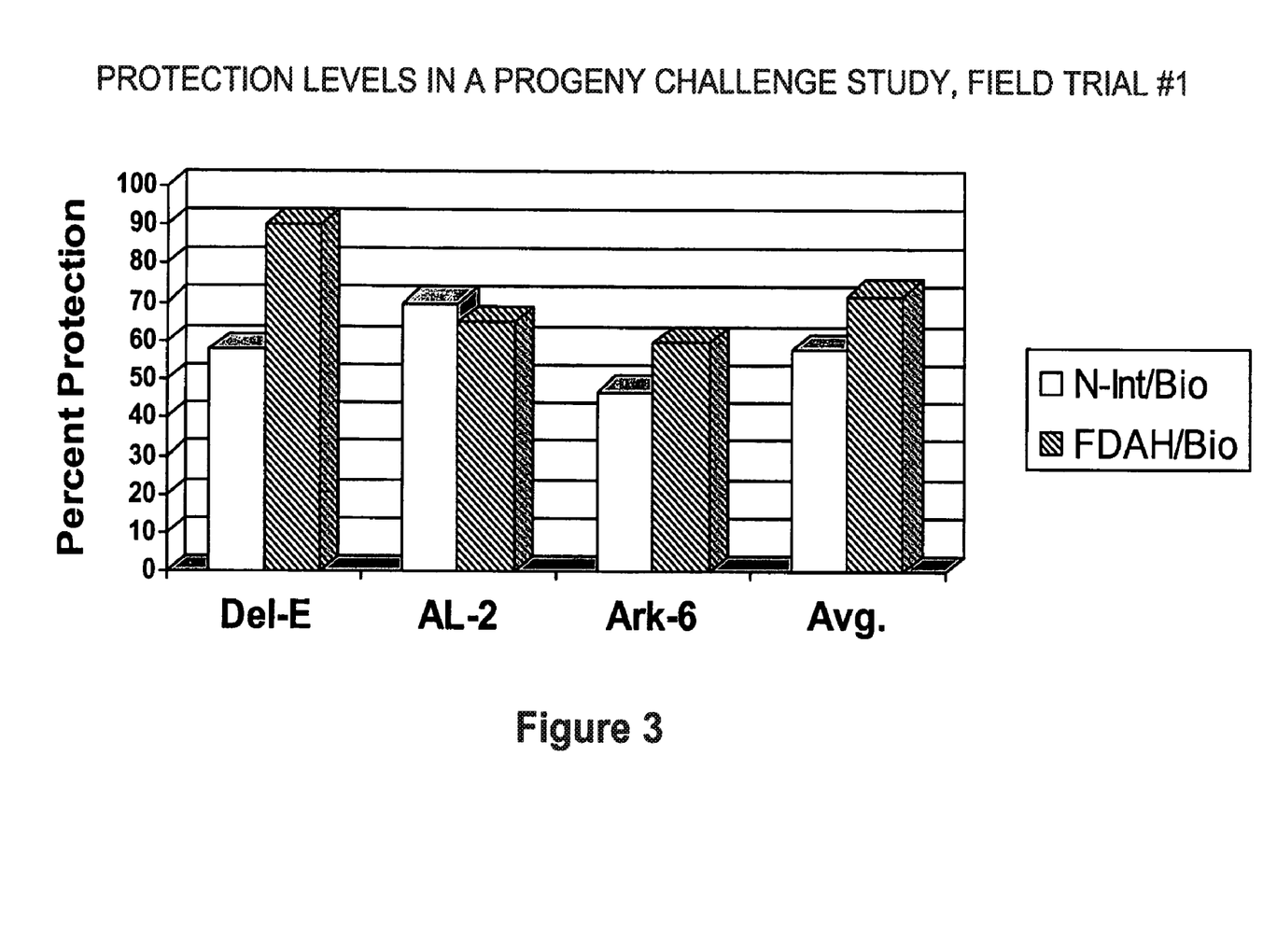
FIG. 3 depicts the percent protection levels observed in a progeny challenge study, field trial #1, using a vaccine composition of the invention and a commercial vaccine.
Figure 4:
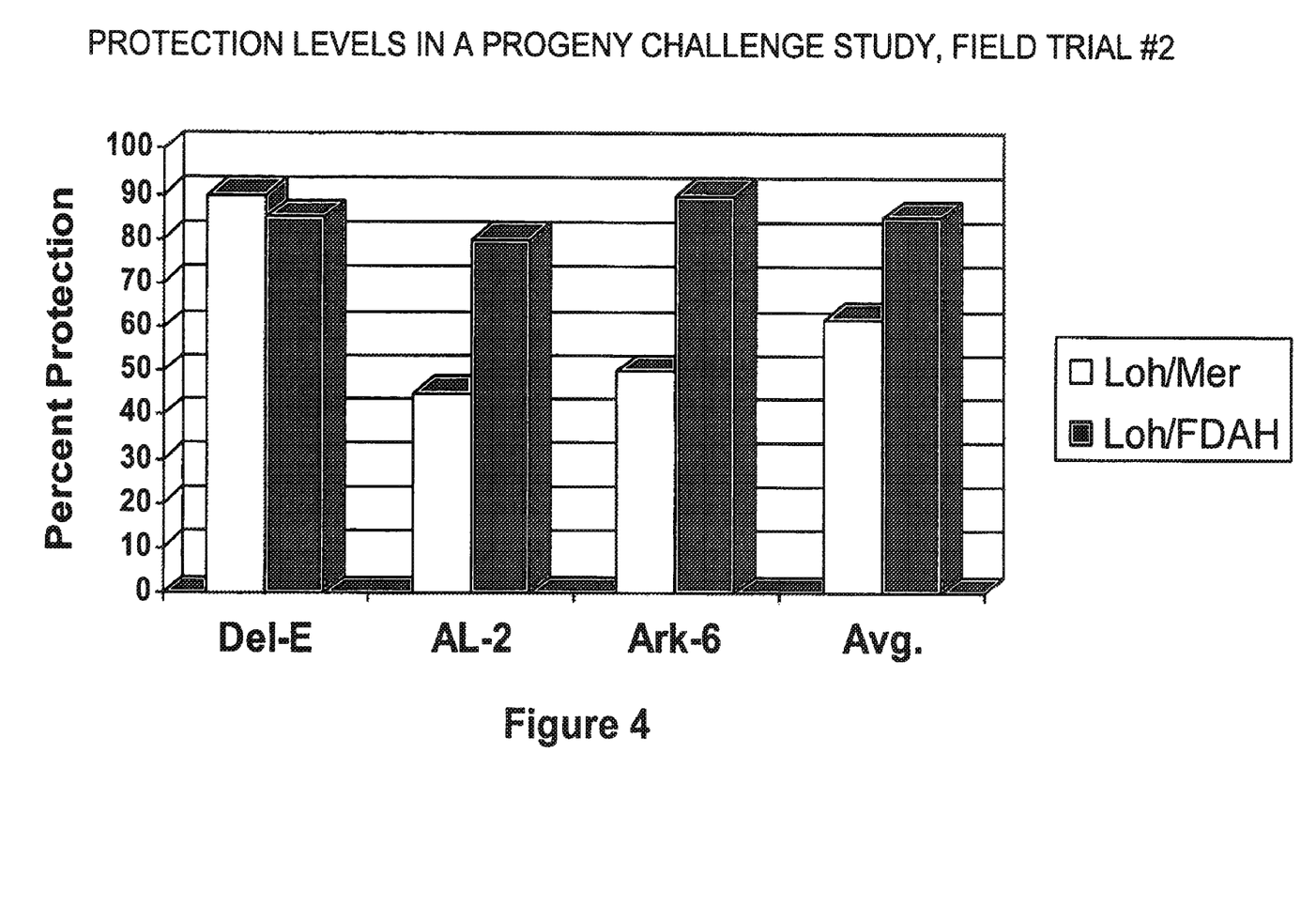
FIG. 4 depicts the percent protection levels observed in a progeny challenge study, field trial #2, using a vaccine composition of the invention and a commercial vaccine.

As depicted in FIGS. 3 and 4, the vaccine composition of the invention was further compared in broiler progeny challenge studies. In each field trial, the standard program consisting of two shots of commercial vaccines was compared to a program whereby the vaccine composition of the invention replaced one of the commercial vaccines. The broiler breeder sources were 38-44 weeks of age when fertile eggs were collected for the study. The results are graphed in terms of percent protection. In FIGS. 3 and 4, the results on the right represent the vaccine program containing the composition of the invention.

While the invention has been described in each of its various embodiments, it is expected that certain modifications thereto may be undertaken and effected by the person skilled in the art without departing from the true spirit and scope of the invention, as set forth in the previous description and as further embodied in the following claims.

What is claimed is:

1. An isolated amino acid sequence comprising SEQ ID NO: 6.

2. The amino acid sequence of claim 1 consisting of SEQ ID NO: 6.

3. A fragment of an Infectious Bursal Disease Virus (IBDV) Viral Protein 2 (VPL2) comprising the amino acid sequence of claim 1.

4. A composition comprising an isolated Infectious Bursal Disease Virus (IBDV) comprising SEQ ID NO: 6.

5. The composition of claim 4 further comprising at least one additional antigenic amino acid sequence.

6. The composition of claim 5, wherein the at least one additional antigenic amino acid sequence is, selected from the group consisting of chicken herpes virus antigens, chicken anemia virus (CAV) antigens, Newcastle Disease virus antigens, Infectious Brochitis (IB) virus antigens, and Infectious Bursal Disease Virus (IBDV) variant antigens.

7. The composition of claim 6, wherein the at least one additional antigenic amino acid sequence is a reovirus antigen.

8. An immunogenic composition comprising the amino acid sequence according to claim 1.

9. A method for inducing protection against infection from Infectious Bursal Disease Virus, which comprises administering to a poultry an composition according to claim 4.

* * * * *